(12) United States Patent
Zhu

(10) Patent No.: US 9,883,699 B2
(45) Date of Patent: *Feb. 6, 2018

(54) HEATING ELEMENT FOR REPLACEABLE VAPORIZER ASSEMBLY AND ELECTRONIC CIGARETTES

(71) Applicant: Xiaochun Zhu, Shenzhen (CN)

(72) Inventor: Xiaochun Zhu, Shenzhen (CN)

(73) Assignee: Shenzhen Kanger Technologies Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/203,795

(22) Filed: Jul. 7, 2016

(65) Prior Publication Data

US 2018/0007964 A1    Jan. 11, 2018

(51) Int. Cl.
*A24F 47/00* (2006.01)
*H05B 3/42* (2006.01)

(52) U.S. Cl.
CPC ............. *A24F 47/008* (2013.01); *H05B 3/42* (2013.01); *H05B 2203/021* (2013.01)

(58) Field of Classification Search
None
See application file for complete search history.

(56) References Cited

U.S. PATENT DOCUMENTS

| | | | | |
|---|---|---|---|---|
| 9,078,474 B2* | 7/2015 | Thompson | ............ | A24F 47/008 |
| 9,101,729 B2* | 8/2015 | Liu | ........ | A61M 15/06 |
| 2016/0295923 A1* | 10/2016 | Lin | ........ | A24F 47/008 |
| 2017/0086506 A1* | 3/2017 | Rado | ........ | A24F 47/008 |

* cited by examiner

*Primary Examiner* — Tho D Ta
(74) *Attorney, Agent, or Firm* — Ming Jiang; M M IP Services LLC

(57) ABSTRACT

Present disclosure relates to a heating tube, a replaceable vaporizer assembly and an electronic cigarette having the replaceable vaporizer assembly. In certain embodiments, the electronic cigarette may include an electronic cigarette body, and a replaceable vaporizer assembly. The electronic cigarette body may include a mouthpiece installed in a mouthpiece base, a connector base, a mounting base defining multiple air intake openings, an E-liquid storage tank, and a connector. The mounting base and the connector base are threadedly connected through an internal thread of mounting base and an external thread of connector base to form an air chamber inside the mounting base and connector base. When in operation, outside air enters the air chamber through the multiple air intake openings and is vaporized by the replaceable vaporizer assembly, goes up through multiple air gaps between the mounting base and the connector base, and exits the electronic cigarette body through the mouthpiece.

20 Claims, 7 Drawing Sheets

HEATING ELEMENT FOR REPLACEABLE VAPORIZER ASSEMBLY AND ELECTRONIC CIGARETTES

FIELD

The present disclosure generally relates to the field of electronic cigarette, and more particularly to heating elements, replaceable vaporizer assemblies having the heating elements and electronic cigarettes having the replaceable vaporizer assemblies.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

It is well known that smoking cigarette is harmful to smoker's health. The active ingredient in a cigarette is mainly nicotine. During smoking, nicotine, along with tar aerosol droplets produced in the cigarette burning, are breathed into the alveolus and absorbed quickly by the smoker. Once nicotine is absorbed into the blood of the smoker, nicotine then produces its effect on the receptors of the smoker's central nervous system, causing the smoker relax and enjoy an inebriety similar to that produced by an exhilarant.

The electronic cigarette is sometimes referred as electronic vaporing device, personal vaporizer (PV), or electronic nicotine delivery system (ENDS). It is a battery-powered device which simulates tobacco smoking. It generally uses a heating element that vaporizes a liquid solution (e-liquid). Some solutions contain a mixture of nicotine and a variety of flavorings, while others release a flavored vapor without nicotine. Many are designed to simulate smoking experience, such as cigarette smoking or cigar smoking. Some of them are made with similar appearance, while others are made considerably different in appearance.

Conventional heating elements are made of resistive wire to generate heat and vaporize E-liquid inside a vaporizer. The heating surface of the heating element is usually small, and it is difficult to generate large amount of E-liquid vapor.

Therefore, an unaddressed need exists in the art to address the aforementioned deficiencies and inadequacies.

SUMMARY

In one aspect, the present disclosure relates to a heating tube. In certain embodiments, the heating tube may include a heating element. The heating element may include a positive terminal and a negative terminal. The positive terminal is electrically coupled to a positive terminal of a power supply, and the negative terminal is electrically coupled to a negative terminal of the power supply. When the power supply is switched on, the heating element is energized by the power supply to heat E-liquid around the heating element to produce E-liquid vapor for an electronic cigarette.

In certain embodiments, the heating element is made of resistive electrical conductive materials. These materials may have large contact area with the E-liquid storage medium to increase amount of E-liquid vapor generated. The heating element may include multiple heating elements to increase amount of E-liquid vapor generated. In certain embodiments, the heating element 111 may include a grid shaped heating element, a mesh shaped heating element, a spiral heating element, a net shaped heating element, and any combination of these shapes.

In another aspect, the present disclosure relates to a replaceable vaporizer assembly. In certain embodiments, the replaceable vaporizer assembly may include: an E-liquid storage medium and a heating tube. The heating tube may include a heating element, a positive terminal, and a negative terminal. The positive terminal is electrically coupled to a positive terminal of a power supply, and the negative terminal is electrically coupled to a negative terminal of the power supply. The E-liquid storage medium is in communication with E-liquid from an E-liquid storage tank such that the E-liquid storage medium is soaked with the E-liquid. When the power supply is switched on the heating element is energized by the power supply to heat E-liquid soaked in the E-liquid storage medium to produce E-liquid vapor for an electronic cigarette.

In one embodiment, the E-liquid storage medium may be a cylindrical E-liquid storage medium installed outside the heating tube. In another embodiment, the E-liquid storage medium may be a round E-liquid storage medium installed inside the heating tube. In certain embodiments, the E-liquid storage medium may include: cotton fibers, polypropylene fibers, terylene fibers, nylon fibers, porous ceramic materials, and any combinations of these materials.

In yet another aspect, the present disclosure relates to an electronic cigarette. In certain embodiments, the electronic cigarette may include an electronic cigarette body, and a replaceable vaporizer assembly. The electronic cigarette body may include a mouthpiece installed in a mouthpiece base, a connector base, a mounting base, an E-liquid storage tank, and a connector.

In certain embodiments, the mounting base may define multiple air intake openings. The mounting base and the connector base are threadedly connected through a first internal thread of the mounting base and an external thread of the connector base to form an air chamber inside of the mounting base and the connector base. When in operation, outside air enters the air chamber through the multiple air intake openings and is vaporized by the replaceable vaporizer assembly, goes up through multiple air gaps between the mounting base and the connector base, and exits the electronic cigarette body through the mouthpiece.

These and other aspects of the present disclosure will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the disclosure and, together with the written description, serve to explain the principles of the disclosure. Wherever possible, the same reference numbers are used throughout the drawings to refer to the same or like elements of an embodiment. The drawings do not limit the present disclosure to the specific embodiments disclosed and described herein. The drawings are not necessarily to scale, emphasis instead being placed upon clearly illustrating the principles of the disclosure, and wherein.

DETAILED DESCRIPTION

Figure 1:
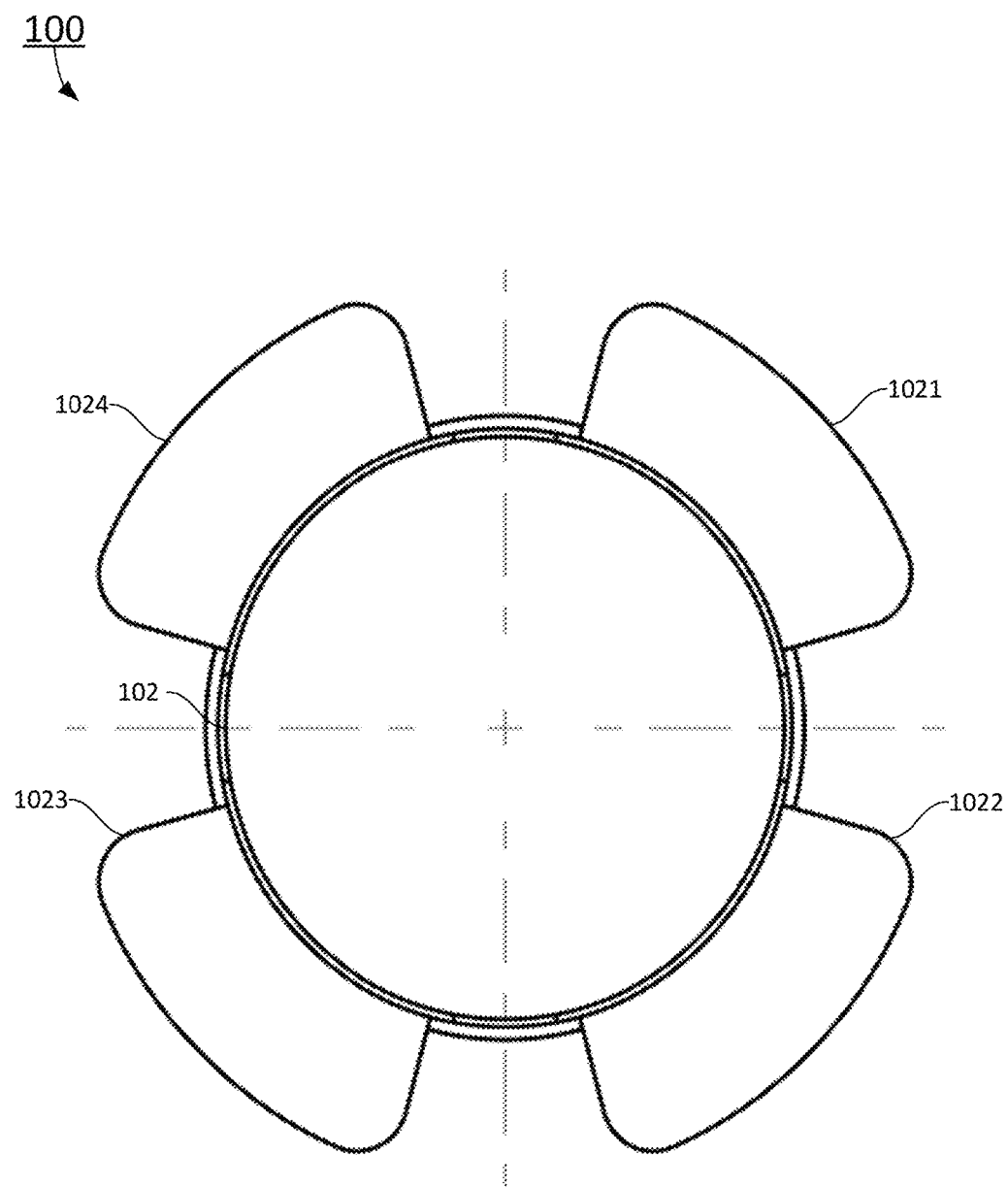
FIG. 1 is a top view of an exemplary heating tube according to certain embodiments of the present disclosure.

The present disclosure will now be described more fully hereinafter with reference to the accompanying drawings, in which exemplary embodiments of the disclosure are shown. This disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom", "upper" or "top," and "front" or "back" may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximates, meaning that the term "around", "about" or "approximately" can be inferred if not expressly stated.

Many specific details are provided in the following descriptions to make the present disclosure be fully understood, but the present disclosure may also be implemented by using other manners different from those described herein, so that the present disclosure is not limited by the specific embodiments disclosed in the following.

The description will be made as to the embodiments of the present disclosure in conjunction with the accompanying drawings FIGS. 1 through 7.

Figure 2:
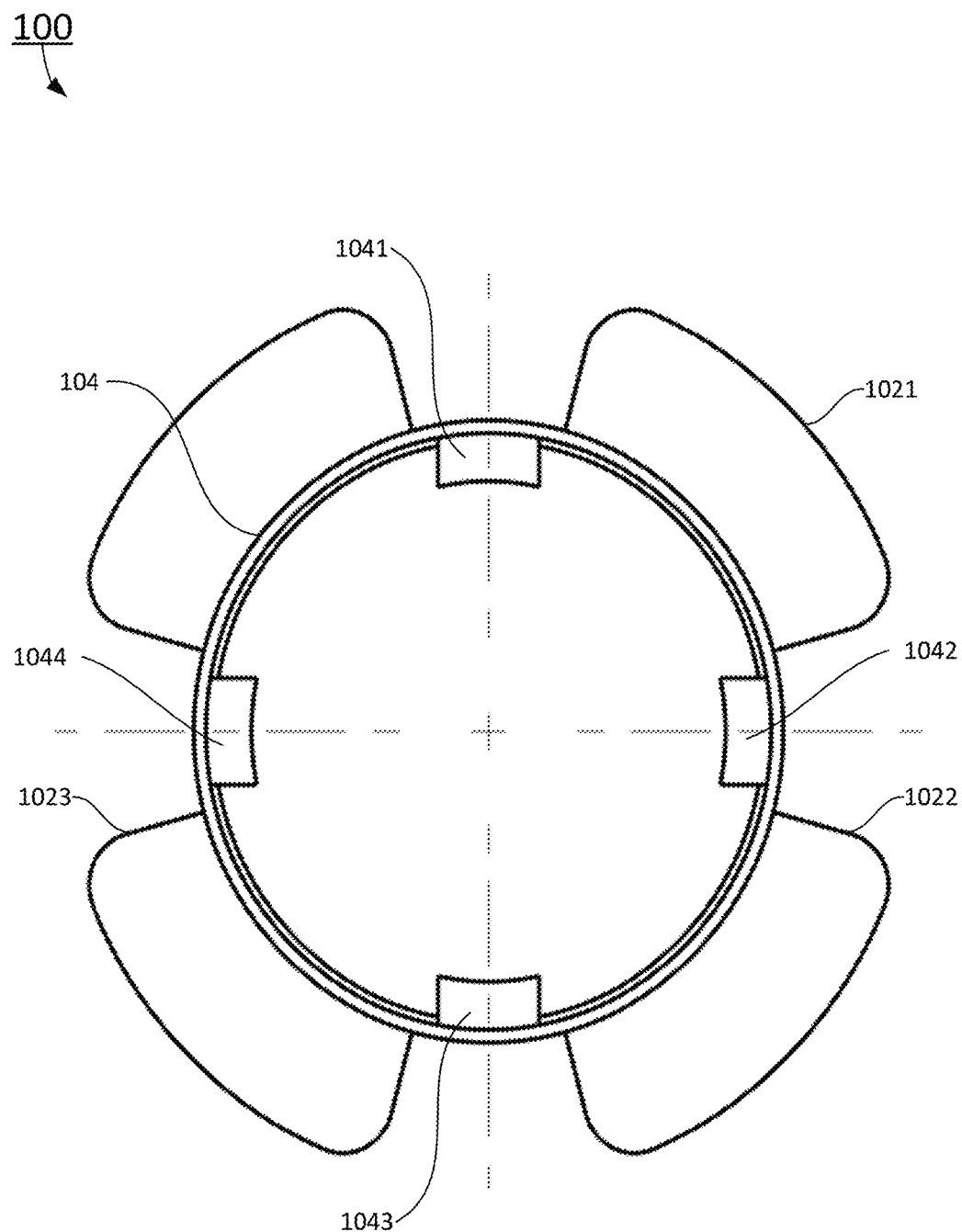
FIG. 2 is a bottom view of the exemplary heating tube according to certain embodiments of the present disclosure.
Figure 3:
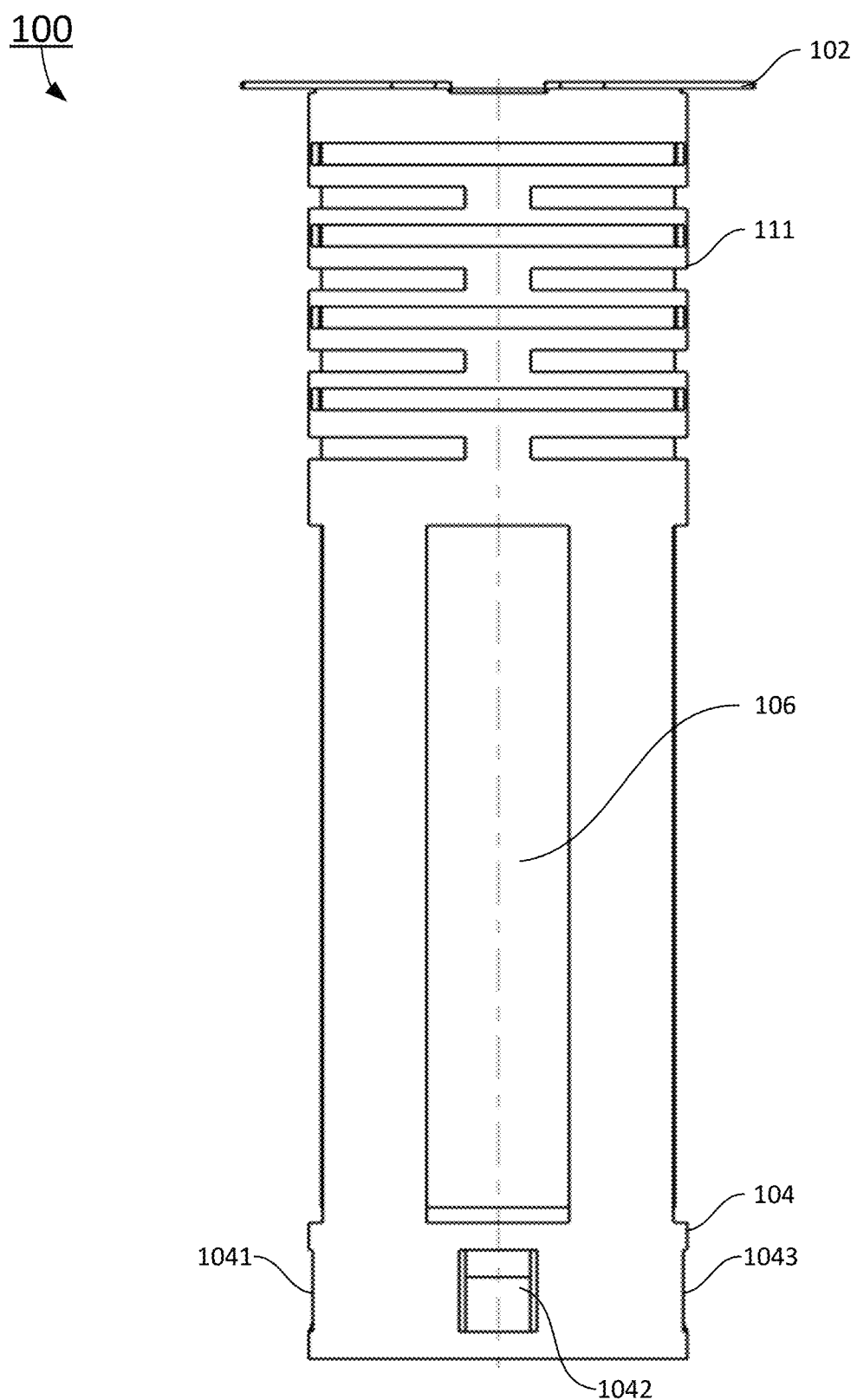
FIG. 3 is a side view of the exemplary heating tube according to certain embodiments of the present disclosure.

In one aspect, the present disclosure relates to a heating tube 100. Referring now to FIGS. 1-3, a top view, a bottom view, and a side view of an exemplary heating tube 100 are shown respectively according to certain embodiments of the present disclosure.

In certain embodiments, the heating tube 100 may include a heating element 11, a positive terminal 102 and a negative terminal 104. In one embodiment, the positive terminal 102 may include four positive terminal contacts: a first positive terminal contact 1021, a second positive terminal contact 1022, a third positive terminal contact 1023, and a fourth positive terminal contact 1024 as shown in FIG. 1. In another embodiment, the negative terminal 104 may include four negative terminal contacts: a first negative terminal contact 1041, a second negative terminal contact 1042, a third negative terminal contact 1043, and a fourth negative terminal contact 1044 as shown in FIG. 2. The positive terminal 102 is electrically coupled to a positive terminal of a power supply, and the negative terminal 104 is electrically coupled to a negative terminal of the power supply. When the power supply is switched on, the heating element 111 is energized by the power supply to heat E-liquid around the heating element 111 to produce E-liquid vapor for an electronic cigarette.

In certain embodiments, the heating tube 100 may include an E-liquid storage medium 106 as shown in FIG. 3. The E-liquid storage medium 106 is in communication with E-liquid from an E-liquid storage tank such that the E-liquid storage medium 106 is soaked with the E-liquid.

In one embodiment, the E-liquid storage medium 106 may be a cylindrical E-liquid storage medium 106. The cylindrical E-liquid storage medium 106 may be installed outside of the heating tube 100. In another embodiment, the E-liquid storage medium 106 may be a round E-liquid storage medium 106. The round E-liquid storage medium 106 may be installed inside the heating tube 100.

In certain embodiments, the E-liquid storage medium 106 may include: cotton fibers, polypropylene fibers, terylene fibers, nylon fibers, porous ceramic materials, and any combinations of these materials.

In certain embodiments, the heating element 111 is made of resistive electrical conductive materials. These materials may have large contact area with the E-liquid storage medium 106 to increase amount of E-liquid vapor generated as shown in FIG. 3.

Figure 4:
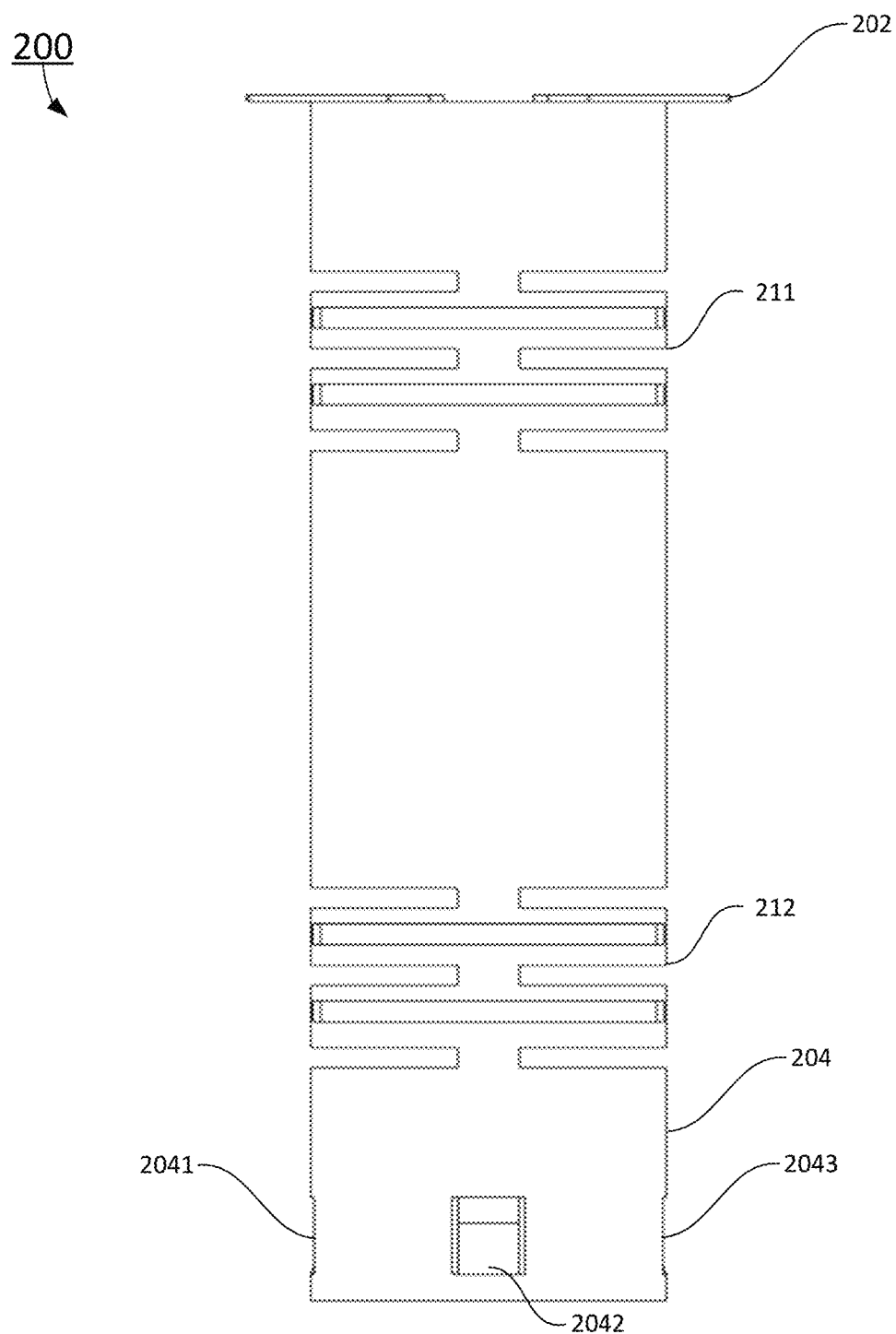
FIG. 4 is a side view of an exemplary heating tube having two heating elements according to certain embodiments of the present disclosure.
Figure 5:
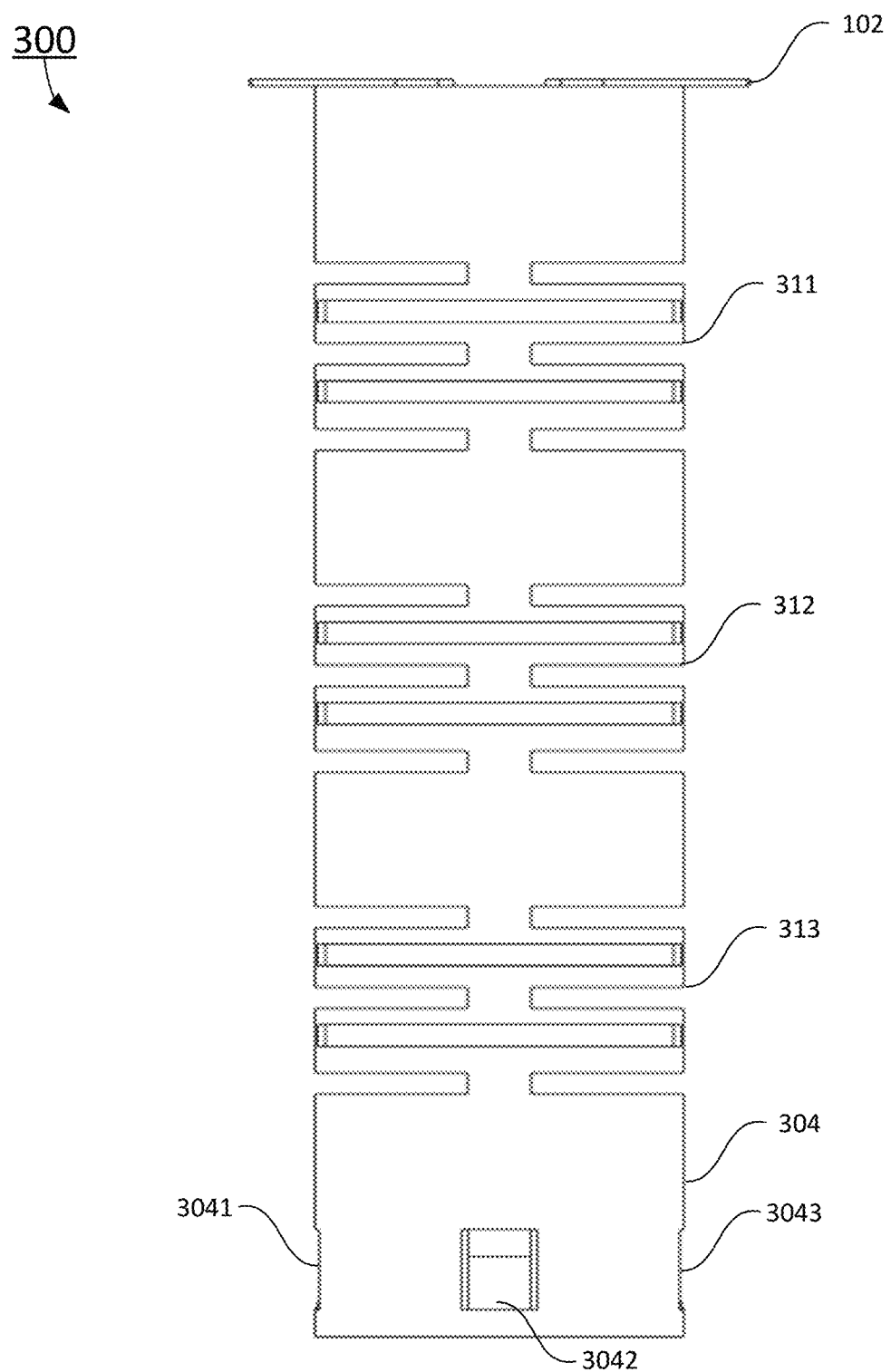
FIG. 5 is a side view of the an exemplary heating tube having three heating elements according to certain embodiments of the present disclosure.

In certain embodiments, the heating element 111 may include multiple heating elements to increase amount of E-liquid vapor generated. In one embodiment as shown in FIG. 4, a heating tube 200 may include two heating elements: a first heating element 211 and a second heating element 212. The first heating element 211 is positioned at a top portion of the heating tube 200, and the second heating element 212 is positioned at a bottom portion of the heating tube 200. In another embodiment as shown in FIG. 5, a heating tube 300 may include three heating elements: a first heating element 311, a second heating element 312, and a third heating element 313. The first heating element 311 is positioned at a top portion of the heating tube 300. The second heating element 312 is positioned at a middle portion of the heating tube 300. The third heating element 313 is positioned at a bottom portion of the heating tube 300.

In one embodiment, these multiple heating elements may be electrically coupled in serial as shown in FIG. 4 and FIG. 5. In another embodiment, these multiple heating elements may be electrically coupled in parallel.

In certain embodiments, the heating element 111 may include a grid shaped heating element, a mesh shaped heating element, a spiral heating element, a net shaped heating element, and any combination of these shapes.

Figure 6:
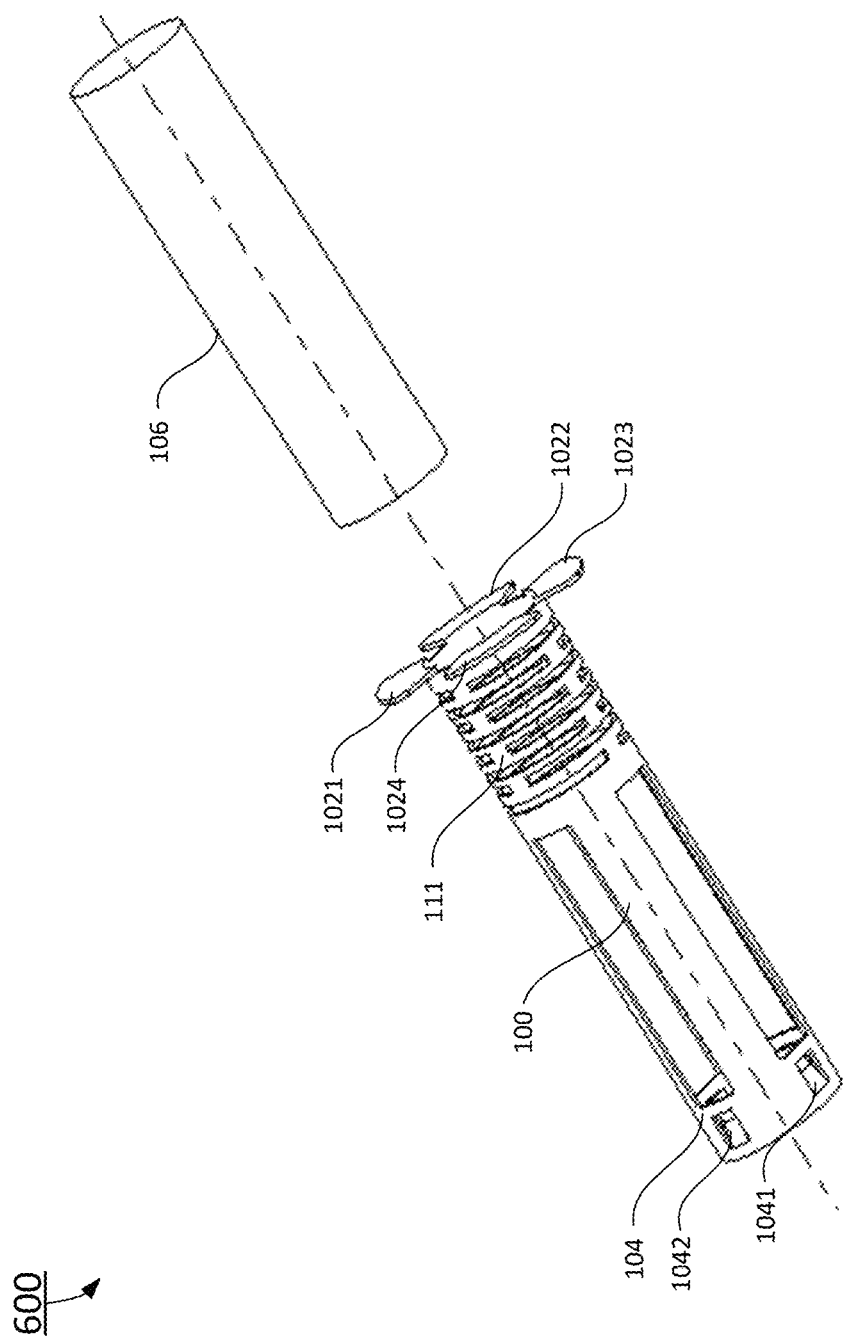
FIG. 6 shows an exploded perspective view of a replaceable vaporizer assembly having the heating tube according to certain embodiments of the present disclosure.

In another aspect, the present disclosure relates to a replaceable vaporizer assembly 600 as shown in FIG. 6. In certain embodiments, the replaceable vaporizer assembly 600 may include: an E-liquid storage medium 106 and a heating tube 100. The heating tube 100 may include a heating element 111, a positive terminal 102, and a negative terminal 104. The positive terminal 102 is electrically coupled to a positive terminal of a power supply, and the negative terminal 104 is electrically coupled to a negative terminal of the power supply. The E-liquid storage medium 106 is in communication with E-liquid from an E-liquid storage tank such that the E-liquid storage medium 106 is soaked with the E-liquid. When the power supply is switched on the heating element 111 is energized by the power supply to heat E-liquid soaked in the E-liquid storage medium 106 to produce E-liquid vapor for an electronic cigarette.

In one embodiment, the E-liquid storage medium 106 may be a cylindrical E-liquid storage medium 106. The cylindrical E-liquid storage medium 106 may be installed outside of the heating tube 100. In another embodiment, the E-liquid storage medium 106 may be a round E-liquid storage medium 106. The round E-liquid storage medium 106 may be installed inside the heating tube 100.

In certain embodiments, the E-liquid storage medium 106 may include: cotton fibers, polypropylene fibers, terylene fibers, nylon fibers, porous ceramic materials, and any combinations of these materials.

In certain embodiments, the heating element 111 is made of resistive electrical conductive materials. These materials may have large contact area with the E-liquid storage medium 106 to increase amount of E-liquid vapor generated.

In certain embodiments, the heating element 111 may include multiple heating elements to increase amount of E-liquid vapor generated. In one embodiment, these multiple heating elements may be electrically coupled in serial. In another embodiment, these multiple heating elements may be electrically coupled in parallel.

In certain embodiments, the heating element 111 may be formed at a bottom portion, a middle portion, and/or a top portion of the heating tube 100.

In certain embodiments, the heating element 111 may include a grid shaped heating element, a mesh shaped heating element, a spiral heating element, a net shaped heating element, and any combination of these shapes.

Figure 7:
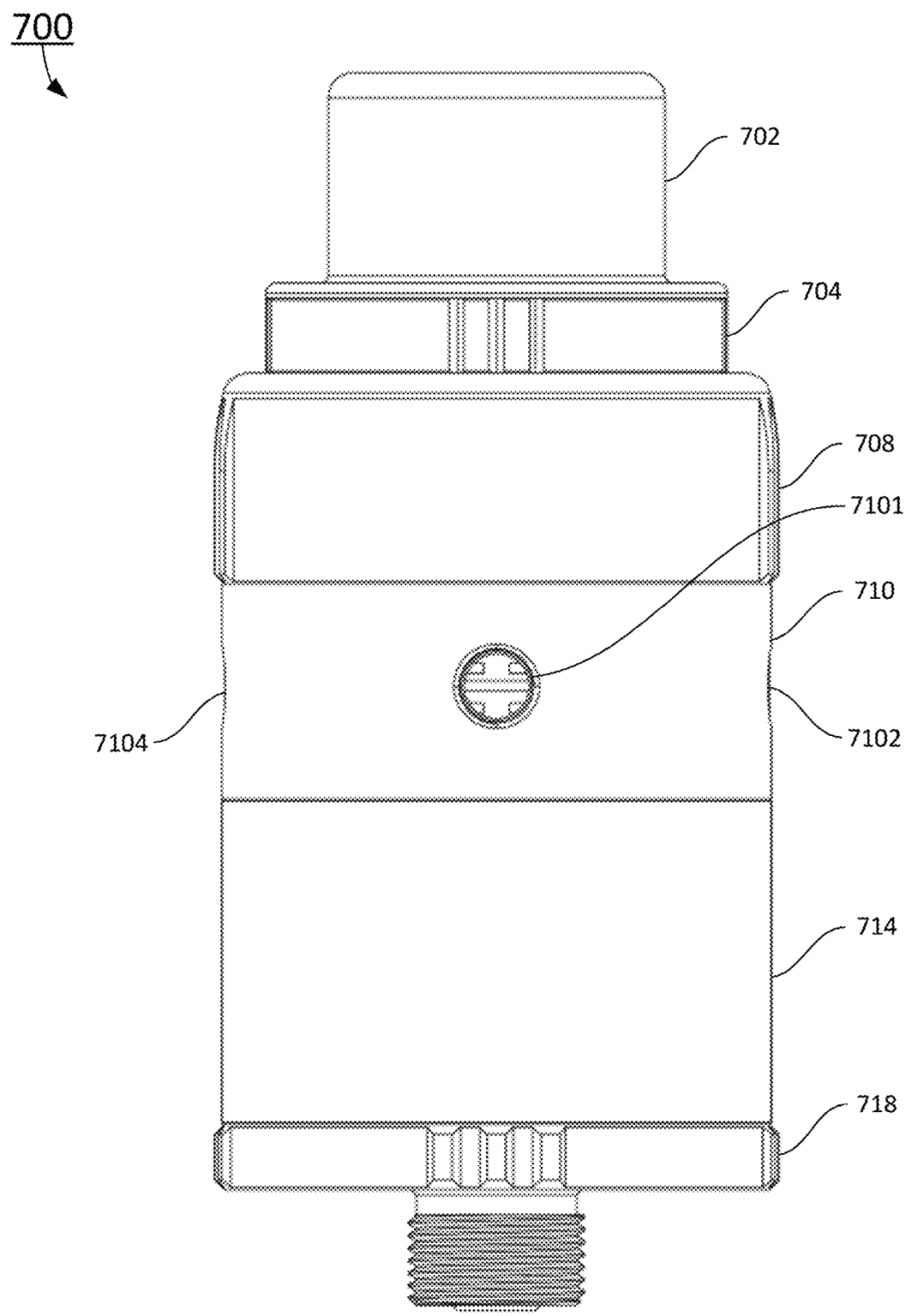
FIG. 7 shows an external view of an electronic cigarette having the replaceable vaporizer assembly and the heating tube according to certain embodiments of the present disclosure.

In yet another aspect, the present disclosure relates to an electronic cigarette. In certain embodiments, the electronic cigarette may include an electronic cigarette body 700 as shown in FIG. 7, and a replaceable vaporizer assembly 600 as shown in FIG. 6. The electronic cigarette body 700 may include a mouthpiece 702 installed in a mouthpiece base 704, a connector base 708, a mounting base 710, an E-liquid storage tank 714, and a connector 718.

In certain embodiments, the mounting base 710 may define multiple air intake openings 7101, 7102, . . . , 710N, where N is a positive integer. In one embodiment as shown in FIG. 7, N is 4. The mounting base 710 may define a first air intake opening 7101, a second air intake opening 7102, a third air intake opening 7103, and a fourth air intake opening 7104. The mounting base 710 and the connector base 708 are threadedly connected through a first internal thread of the mounting base 710 and an external thread of the connector base 708 to form an air chamber 150 inside of the mounting base 710 and the connector base 708. When in operation, outside air enters the air chamber 150 through the multiple air intake openings and is vaporized by the replaceable vaporizer assembly 600, goes up through multiple air gaps between the mounting base 710 and the connector base 708, and exits the electronic cigarette body 700 through the mouthpiece 702.

In certain embodiments, the replaceable vaporizer assembly 600 may include: an E-liquid storage medium 106, and the heating tube 100. The heating tube 100 may include a heating element 111, a positive terminal 102, and a negative terminal 104. The positive terminal 102 is electrically coupled to a positive terminal of the power module, and the negative terminal 104 is electrically coupled to a negative terminal of the power module. When the power module is switched on the heating element is energized by the power module to heat E-liquid stored in the E-liquid storage medium 106 to produce E-liquid vapor for the electronic cigarette.

In certain embodiments, the heating element 111 may include multiple heating elements to increase amount of E-liquid vapor generated. In one embodiment, the multiple heating elements may be electrically coupled in serial. In another embodiment, the multiple heating elements may be electrically coupled in parallel.

In certain embodiments, the heating element 111 is made of resistive electrical conductive materials having large contact area with the E-liquid storage medium 206 to increase amount of E-liquid vapor generated. In certain embodiments, the heating element 111 may include: a grid shaped heating element, a mesh shaped heating element, a net shaped heating element, a spiral heating element, and any combinations of these shapes.

In certain embodiments, the E-liquid storage medium may include a cylindrical E-liquid storage medium 206 and a round E-liquid storage medium 206. The cylindrical E-liquid storage medium 206 may be installed outside of the heating element 111. The round E-liquid storage medium 206 may be installed inside of the heating element 111.

In certain embodiments, the E-liquid storage medium 206 may include cotton fibers, polypropylene fibers, terylene fibers, nylon fibers, porous ceramic materials, and any combination of these materials.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims, the foregoing description and the exemplary embodiments described therein, and accompanying drawings.

What is claimed is:

1. A heating tube, comprising:
   a plurality of tubular heating elements, coaxially positioned outside of an E-liquid storage tube for heating E-liquid stored in the E-liquid storage tube, wherein the heating tube comprises a positive terminal electrically coupled to a positive terminal of a power supply, and a negative terminal electrically coupled to a negative terminal of the power supply, when the power supply is switched on the heating tube is energized by the power supply to heat E-liquid around the heating tube to produce E-liquid vapor for an electronic cigarette.

2. The heating tube of claim 1, wherein the E-liquid storage tube is in communication with E-liquid from an E-liquid storage tank such that the E-liquid storage tube is soaked with the E-liquid.

3. The heating tube of claim 2, wherein the E-liquid storage tube comprises:
   an E-liquid storage tube coaxially wrapped around on an exterior surface of the heating tube, or
   an E-liquid storage tube coaxially attached to an interior surface of the heating tube.

4. The heating tube of claim 2, wherein the E-liquid storage tube comprises:
   cotton fibers;
   polypropylene fibers;
   terylene fibers;
   nylon fibers; and
   porous ceramic materials.

5. The heating tube of claim 2, wherein each of the plurality of tubular heating elements is made of resistive electrical conductive materials having large contact area with the E-liquid storage tube to increase amount of E-liquid vapor generated.

6. The heating tube of claim 1, wherein the plurality of tubular heating elements is electrically coupled in serial to increase amount of E-liquid vapor generated.

7. The heating tube of claim 1, wherein each of the plurality of tubular heating elements may be formed at a bottom portion, a middle portion, and/or a top portion of the heating tube.

8. The heating tube of claim 1, wherein each of the plurality of tubular heating elements comprises:
   a grid shaped heating element;
   a mesh shaped heating element;
   a spiral heating element;
   a net shaped heating element; and
   any combination thereof.

9. A replaceable vaporizer assembly, comprising:
   an E-liquid storage tube for receiving and storing E-liquid from an E-liquid storage tank, wherein a hollow cavity of the E-liquid storage tube forms an E-liquid vapor passage; and
   a heating tube having a plurality of tubular heating elements coaxially wrapped around on an exterior surface of the E-liquid storage tube, a positive terminal, and a negative terminal, wherein the positive terminal is electrically coupled to a positive terminal of a power supply, and the negative terminal is electrically coupled to a negative terminal of the power supply, when the power supply is switched on the heating tube is energized by the power supply to heat E-liquid soaked in the E-liquid storage tube to produce E-liquid vapor for an electronic cigarette.

10. The replaceable vaporizer assembly of claim 9, wherein the E-liquid storage tube comprises:
    an E-liquid storage tube coaxially wrapped around on an exterior surface of the heating tube, or
    an E-liquid storage tube coaxially attached to an interior surface of the heating tube, wherein the E-liquid storage tube comprises:
    cotton fibers;
    polypropylene fibers;
    terylene fibers;
    nylon fibers; and
    porous ceramic materials.

11. The replaceable vaporizer assembly of claim 9, wherein the plurality of tubular heating elements is electrically coupled in serial to increase amount of E-liquid vapor generated.

12. The replaceable vaporizer assembly of claim 9, wherein each of the plurality of tubular heating elements is formed at a bottom portion, a middle portion, and/or a top portion of the heating tube.

13. The replaceable vaporizer assembly of claim 9, wherein each of the plurality of tubular heating elements is made of resistive electrical conductive materials having large contact area with the E-liquid storage tube to increase amount of E-liquid vapor generated.

14. The replaceable vaporizer assembly of claim 9, wherein each of the plurality of tubular heating elements comprises:
    a grid shaped heating element;
    a mesh shaped heating element;
    a spiral heating element; and
    any combination thereof.

15. An electronic cigarette comprising:
    an electronic cigarette body having a mouthpiece installed in a mouthpiece base, a connector base, a mounting base defining a plurality of air intake openings, an E-liquid storage tank, and a connector; and a replaceable vaporizer assembly having an E-liquid storage tube for receiving and storing E-liquid from an E-liquid storage tank, wherein a hollow cavity of the E-liquid storage tube forms an E-liquid vapor passage; and a heating tube having a plurality of tubular heating elements coaxially wrapped around on an exterior surface of the E-liquid storage tube, a positive terminal, and a negative terminal, wherein the mounting base and the connector base are threadedly connected through a first internal thread of the mounting base and an external thread of the connector base to form an air chamber inside of the mounting base and the connector base, wherein outside air enters the air chamber to be vaporized by the replaceable vaporizer assembly through the plurality of air intake openings, goes up through a plurality of gaps between the mounting base and the connector base, and exits the electronic cigarette body through the mouthpiece, wherein the connector base comprises an internal thread configured to threadedly connect to an external thread of the mouthpiece base, and the external thread, wherein the mounting base comprises the first internal thread configured to threadedly connect to the external thread of the connector base, and a second internal thread, and wherein the connector comprises a first external thread configured to threadedly connect to the second internal thread of the mounting base, and a second external thread configured to threadedly connect to a negative terminal of a power supply.

16. The electronic cigarette of claim 15, wherein the heating tube comprises a plurality of tubular heating elements, a positive terminal, and a negative terminal, wherein the positive terminal is electrically coupled to a positive terminal of the power supply, and the negative terminal is electrically coupled to a negative terminal of the power supply, when the power supply is switched on the heating tube is energized by the power supply to heat E-liquid soaked in the E-liquid storage tube to produce E-liquid vapor for an electronic cigarette.

17. The electronic cigarette of claim 16, wherein the plurality of tubular heating elements is electrically coupled in serial to increase amount of E-liquid vapor generated.

18. The electronic cigarette of claim 16, wherein each of the plurality of tubular heating elements is made of resistive electrical conductive materials having large contact area with the E-liquid storage tube to increase amount of E-liquid vapor generated.

19. The electronic cigarette of claim 16, wherein each of the plurality of tubular heating elements comprises:
 a grid shaped heating element;
 a mesh shaped heating element;
 a spiral heating element; and
 any combination thereof.

20. The electronic cigarette of claim 16, wherein the E-liquid storage tube comprises:
 an E-liquid storage tube coaxially wrapped around on an exterior surface of the heating tube, and
 an E-liquid storage tube coaxially attached to an interior surface of the heating tube, wherein the E-liquid storage tube comprises:
 cotton fibers;
 polypropylene fibers;
 terylene fibers;
 nylon fibers;
 porous ceramic materials; and
 any combination thereof.

* * * * *